(12) United States Patent
Freund (10) Patent No.: US 7,823,219 B2
(45) Date of Patent: Nov. 2, 2010

(54) DECUBITUS ULCER PREVENTION AND TREATMENT

(75) Inventor: Robert M. Freund, Old Westbury, NY (US)

(73) Assignee: Angiosome, Inc., Greenwich, CT (US)

( * ) Notice: Subject to any disclaimer, the term of this patent is extended or adjusted under 35 U.S.C. 154(b) by 1047 days.

(21) Appl. No.: 10/952,349

(22) Filed: Sep. 27, 2004

(65) Prior Publication Data
US 2006/0064800 A1    Mar. 30, 2006

(51) Int. Cl.
*A41D 13/00* (2006.01)
(52) U.S. Cl. ............................................. 2/69; 2/DIG. 3
(58) Field of Classification Search ................ 2/46, 2/69, 455, 227, 238, 79, 92, 228, 465–467, 2/DIG. 3
See application file for complete search history.

(56) References Cited

U.S. PATENT DOCUMENTS

| | | | |
|---|---|---|---|
| 376,013 | A | 1/1888 | Sandman et al. |
| 2,391,282 | A | 12/1945 | Van Orman |
| 2,392,992 | A | 1/1946 | Martin |
| 2,694,395 | A | 11/1954 | Brown |
| 2,762,047 | A | 9/1956 | Flagg et al. |
| 3,020,910 | A | 2/1962 | Ward |
| 3,071,133 | A | 1/1963 | Eisen |
| 3,589,366 | A * | 6/1971 | Feather .................. 604/312 |
| 3,659,593 | A | 5/1972 | Vail |
| 3,823,711 | A | 7/1974 | Hatton |
| 3,920,006 | A | 11/1975 | Lapidus |
| 4,186,732 | A | 2/1980 | Christoffel |
| 4,331,133 | A | 5/1982 | Arkans |
| 4,372,297 | A | 2/1983 | Perlin |
| 4,492,234 | A | 1/1985 | Arkans |
| 4,567,887 | A | 2/1986 | Couch, Jr. |
| 4,624,248 | A | 11/1986 | Poole et al. |
| 4,637,083 | A | 1/1987 | Goodwin |
| 4,737,994 | A | 4/1988 | Galton |
| 4,738,249 | A | 4/1988 | Linman et al. |
| 4,768,250 | A | 9/1988 | Kato |
| 4,794,659 | A | 1/1989 | Kurita et al. |
| 5,025,781 | A | 6/1991 | Ferrari |
| 5,157,789 | A | 10/1992 | Klass |
| 5,218,954 | A | 6/1993 | Van Bemmelen |
| 5,370,603 | A | 12/1994 | Newman |
| 5,383,842 | A | 1/1995 | Bertini |
| 5,435,009 | A | 7/1995 | Schild et al. |
| 5,545,128 | A * | 8/1996 | Hayes et al. ................ 602/61 |
| 5,575,762 | A | 11/1996 | Peeler et al. |
| 5,584,798 | A | 12/1996 | Fox |
| 5,591,200 | A | 1/1997 | Cone et al. |
| 5,603,690 | A | 2/1997 | Barry |

(Continued)

*Primary Examiner*—Tejash Patel
(74) *Attorney, Agent, or Firm*—Matthew B. Dernier, Esq.; Gibson & Dernier LLP (57) ABSTRACT

A device and method for alleviating pressure on a portion of a patient's body that may be bed-ridden or otherwise constrained for long periods of time. A position of the mechanism is based upon a location or distribution of angiosomes in the body portion. The mechanism includes a pump, and a portable garment with inflatable channels and pressure relievers. The channels provide varying pressure on the body portion, a maximum pressure being set at a level sufficient for treating or preventing decubitus ulcer formation on the body portion. The channels are positioned based upon angiosome distribution in the portion of the body. The pressure relievers protect tissue on bony prominences from excess pressure.

77 Claims, 11 Drawing Sheets

U.S. PATENT DOCUMENTS

| | | |
|---|---|---|
| 5,674,262 A | 10/1997 | Tumey |
| 5,681,339 A | 10/1997 | McEwen et al. |
| 5,688,225 A | 11/1997 | Walker |
| 5,795,312 A | 8/1998 | Dye |
| 5,935,146 A | 8/1999 | McEwen et al. |
| 5,968,073 A | 10/1999 | Jacobs |
| 6,007,559 A | 12/1999 | Arkans |
| 6,009,873 A | 1/2000 | Neviaser |
| 6,010,471 A | 1/2000 | Ben-Noon |
| 6,085,372 A | 7/2000 | James et al. |
| 6,129,688 A | 10/2000 | Arkans |
| 6,290,662 B1 | 9/2001 | Morris et al. |
| 6,334,443 B1 * | 1/2002 | Olsen .................. 128/846 |
| 6,358,219 B1 | 3/2002 | Arkans |
| 6,447,467 B1 | 9/2002 | Barak |
| 6,460,195 B2 * | 10/2002 | Wang .................. 2/228 |
| 6,468,237 B1 | 10/2002 | Lina |
| 6,478,757 B1 | 11/2002 | Barak |
| 6,494,852 B1 | 12/2002 | Barak et al. |
| 6,544,202 B2 | 4/2003 | McEwen et al. |
| 6,585,709 B2 | 7/2003 | Maimets |
| 6,589,194 B1 | 7/2003 | Calderon et al. |
| 6,592,534 B1 | 7/2003 | Rutt et al. |
| 6,772,439 B1 * | 8/2004 | McMullen, Jr. .................. 2/46 |
| 6,892,734 B1 * | 5/2005 | Schleicher et al. .......... 128/889 |
| 7,017,195 B2 * | 3/2006 | Buckman et al. .............. 2/455 |
| 2002/0010446 A1 | 1/2002 | Maimets |

* cited by examiner

DECUBITUS ULCER PREVENTION AND TREATMENT

FIELD OF INVENTION

The present invention relates to a therapeutic pressure-relieving device and method for preventing and treating decubitus ulcers on a portion of a patient's body.

BACKGROUND

Decubitus ulcers (commonly referred to as "bedsores") may form on parts or portions of a patient's body when in contact for a prolonged period of time with an object such as, for example, a bed, a wheelchair, or other type of furniture. The pressure exerted on the skin covering or surrounding the bony prominences on the portions of the patient's body that are in contact with a surface on the furniture may result in the skin becoming inflamed, and may obstruct or restrict the blood flow to the skin and/or the underlying tissue, causing the skin and underlying tissue to become ischemic, eventually resulting in the formation of decubitus ulcers. Decubitus ulcers can form in any area of tissue covering a bony prominence that is in contact with the surface of the bed or sofa or other furniture upon which the patient is resting, e.g., parts of the spine, heels, elbows, and shoulders, shoulder blades, as well as the sacral, trochanteric and ischial areas in the coccyx, hips and buttocks.

Specifically, although arterial inflow can continue and withstand pressure upwards of 170-mm Hg or greater, venous return or blood flow from a region is restricted or obstructed with pressures as low as 32-mm Hg on the skin and underlying tissue. The restriction or obstruction of the venous return of blood from the skin and underlying tissue may lead to the buildup of toxins and waste products that may lead to the formation of decubitus ulcers. Initially, pressure on the skin and tissue may lead to pink coloration and/or mild inflammation, which may disappear within a few hours of relieving pressure on the area. If pressure is not relieved, superficial lesions may form on the skin, then turning into ulcers which continue growing deeper until extending through the bone to internal organs, eventually becoming fatal to the patient.

A traditional means for preventing the formation of decubitus ulcers is to physically turn the patient from side to side at short intervals of time, thus alleviating the amount of time a specific body part is subjected to straining pressures. However, this method of prevention often proves ineffective since the turning of the patient only relieves pressure from certain regions of the body. Moreover, a patient will many times return to a default position even after having been rotated. In addition, since nurses or other aids must be present to physically rotate the patient, this method is laborious, time-consuming and costly.

An alternative method for preventing the formation of decubitus ulcers is the use of air mattresses. Since air mattresses reduce the solidity of the contact surface, the mattresses relieve some of the pressure on the patient's body. However, these devices can be costly and not readily available to all patients. Furthermore, the mattresses are not easily portable in case the patient is moved to another unit or bed.

SUMMARY

This invention relates to a therapeutic device and method for treating and preventing decubitus ulcers on parts or portions of a patient's body by alleviating pressure on the tissue covering and immediately surrounding the bony prominences in the body portion and by alleviating pressure on the blood vessels in the angiosomes in the body portion to allow blood flow to continue throughout the body portion, including venous return, as well as arterial inflow. The device may be configured to act upon a particular body portion. The device may include inflatable channels or pockets positioned within the device based on the distribution of one or more angiosomes in the body portion, and pressure relievers to protect the tissue covering and immediately surrounding the bony prominences in the body portion. The channels may be sequentially or periodically inflated and deflated to alleviate pressure on the body portion while allowing blood flow throughout the angiosomes.

In an example embodiment, the device may include a portable, washable, removable, durable garment that provides pressure relief from sacral, trochanteric and ischial pressure sores or decubitus ulcers. The device may use sequential air channel technology to relieve pressure and allow blood flow to and from the sacral, trochanteric and ischial regions of the coccyx, hips and buttocks based on the angiosome distribution or location of angiosomes in the coccyx, hips and buttocks.

The garment may include rib-shaped or rib-patterned inflatable cushions, pockets or channels radially oriented around a position of an angiosome in each area. The channels are sequentially inflated and deflated to vary and relieve pressure around a center of the angiosome and maximize blood flow around the angiosomes. Air, water or other fluids may be pumped into the channels and removed from the channels with a bedside pump or motor attached to ports that are connected to the channels in the garment. The garment may be made with plastic or another material that may be washable and collapsible for storage purposes. The garment may also be made with a breathable fabric. For example, an inner liner made out of cotton can be provided to line the interior of the garment. The inner liner may be washable and replaceable or disposable. The garment may also have one or more ports to releasably connect the pump or motor to the garment.

The pump or motor can inflate and/or deflate the channels in the garment through the ports on the garment. For example, the garment may have two ports, with each half of the channels in the garment being inflated and deflated by the pump through each of the ports. Specifically, one set of channels may be deflated through one port, while the channels in between the deflated channels are being inflated through the other port.

In an example embodiment, an apparatus includes a portable garment configured to be placed on a portion of a body to provide a varying pressure on the body portion. The provided pressure varying within a range sufficient for at least one of treating and preventing a decubitus ulcer in the body portion.

In an example embodiment, an apparatus includes a mechanism configured to alleviate pressure on a portion of a body. The mechanism provides a varying pressure on the body portion. The mechanism may include channels or pockets that are inflatable with a fluid (e.g., air or water), or with a gel-like substance (e.g., silicon or another pliable material or substance). The pressure provided by the sequential or periodic inflation and deflation of the channels or pockets may vary continuously, e.g., by fluctuating through a range of pressures, or it may vary periodically, providing different levels of pressure at different time periods. The mechanism is positioned based on, inter alia, the location or distribution of one or more angiosomes in the body portion.

In an example embodiment, an apparatus comprises a device including a plurality of inflatable channels configured to be periodically or sequentially inflated and deflated to provide a varying pressure on a portion of a body of a patient that varies within a range sufficient for at least one of treating and preventing a decubitus ulcer.

In an example embodiment, a garment for treating and preventing decubitus ulcers around one or more of the coccygeal, hip and buttocks areas of a patient's body includes one or more cushions in the garment, and one or more adjustable bands removably attaching the garment to the body. The cushions are positioned radially away from one or more of the sacrum, ischial and trochanter areas. The cushions are positioned in the garment as a function of the location or distribution of the angiosomes in one or more of the sacrum, ischial and trochanter areas.

In an example embodiment, an apparatus for treating and preventing decubitus ulcers around at least one of a coccygeal, buttocks and hip areas of a body includes a garment and a pump releasably connectable to the garment. The garment includes a plurality of inflatable channels and a plurality of pressure relievers. The channels are configured to be alternately inflated and deflated in order to provide a variety of pressures on a body portion in or around the coccygeal, buttocks and hip areas of the body. The channels and the pressure relievers are positioned in the garment based on the locations of angiosomes or angiosome distribution in one or more of the sacrum, ischial and trochanter regions in the coccygeal, buttocks and hip areas. The pump is configured to pump and remove air from the inflatable channels in the garment.

In an example embodiment, a method for treating and preventing decubitus ulcers on a portion of a body includes the step of sequentially or periodically inflating and deflating channels in a garment worn on the body portion. The maximum pressure provided by the channels in the garment on the body portion is sufficient to treat and/or prevent decubitus ulcers treating or preventing a decubitus ulcer on the body portion.

In an example embodiment, a method for treating and preventing decubitus ulcers on a portion of the body includes the step of sequentially or periodically inflating and deflating air channels in a garment worn on the body portion. The channels are positioned in the garment as a function of the location of angiosomes in the body portion.

DETAILED DESCRIPTION

Figure 1:
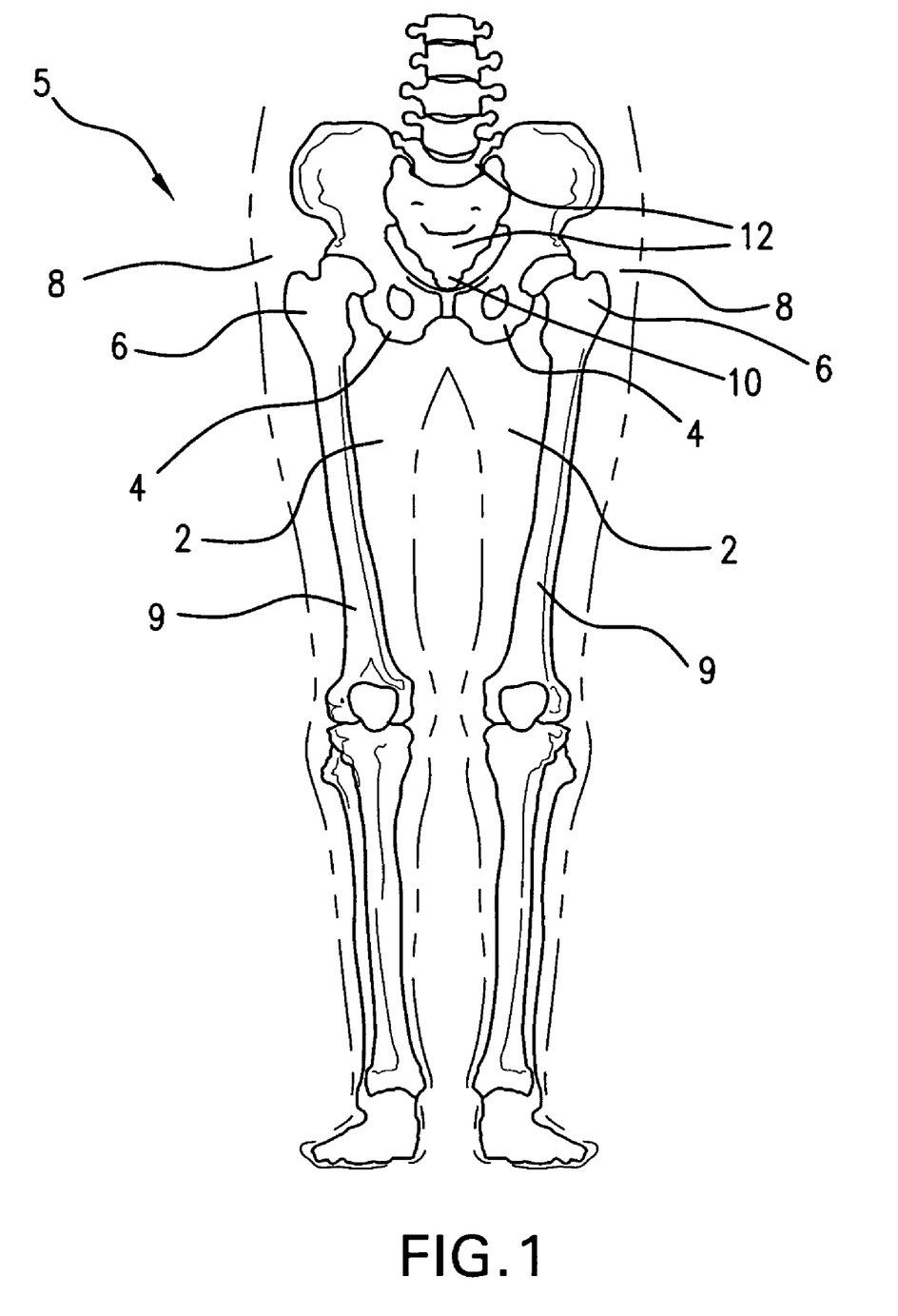
FIG. 1 illustrates a bone structure of a lower portion of a human body.
Figure 2:
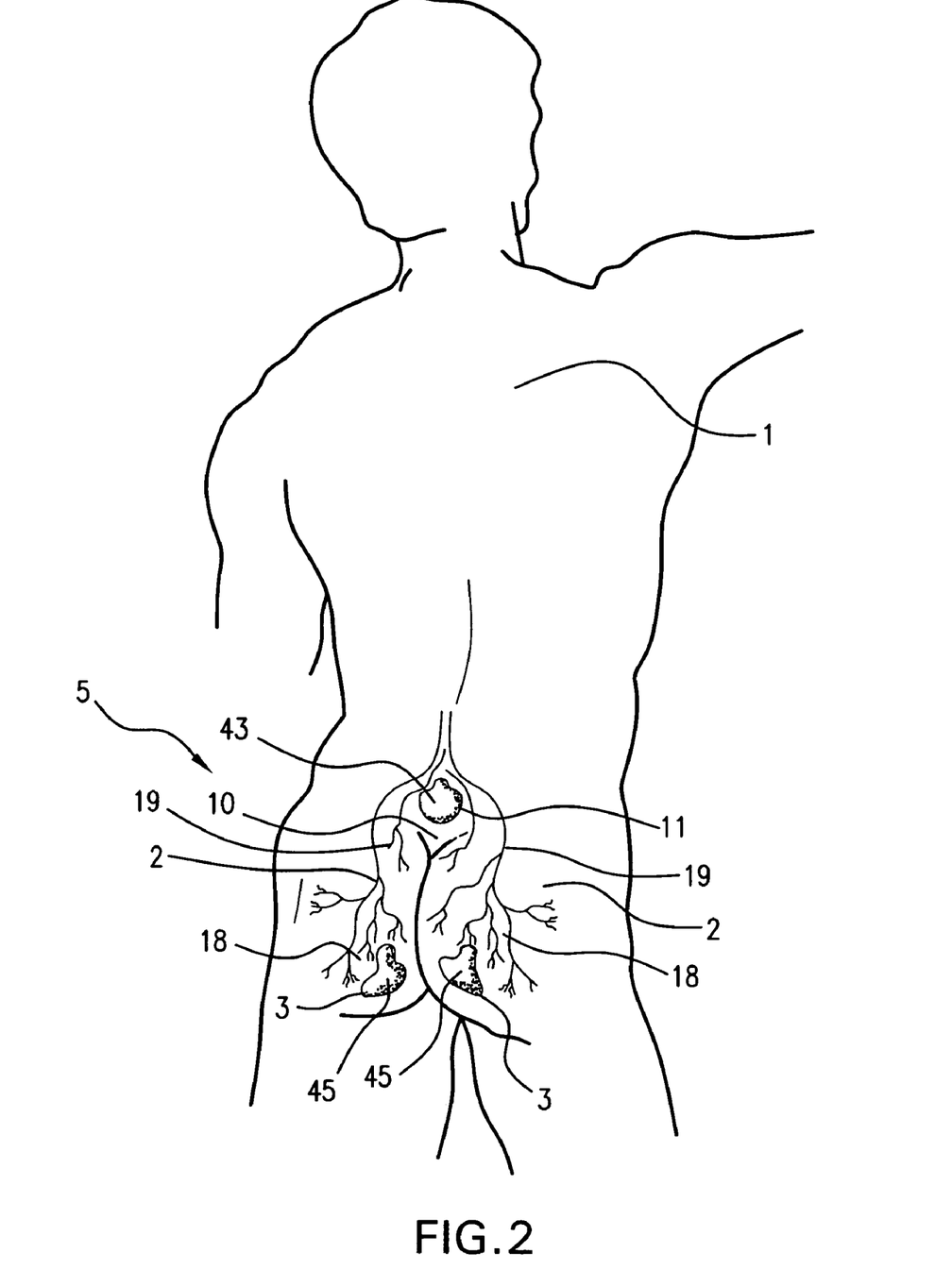
FIG. 2 illustrates angiosome distribution and location, and locations of blood vessels and tissues surrounding bony prominences in the lower portion of a standing human body.
Figure 3:
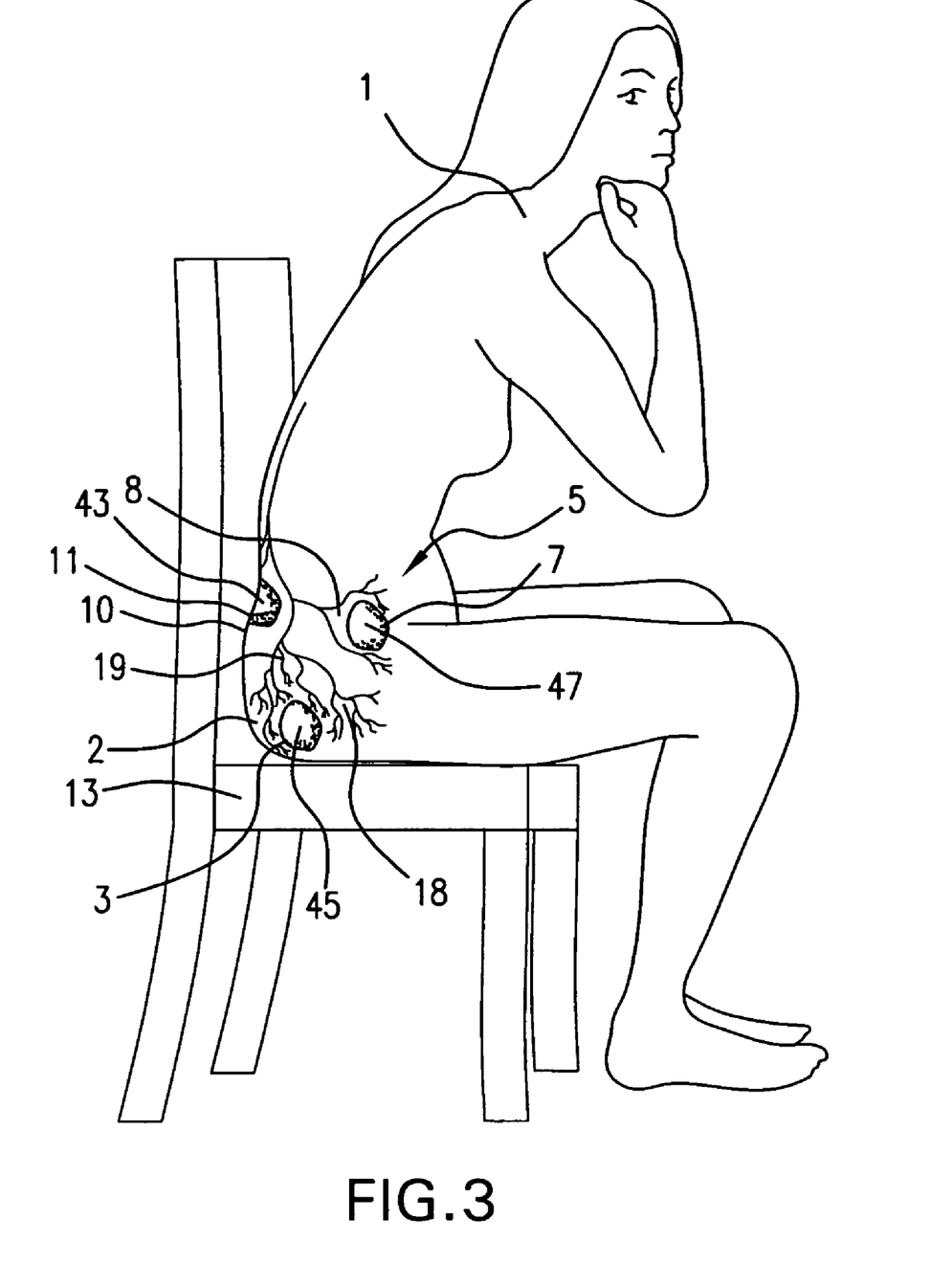
FIG. 3 illustrates angiosome distribution and location, and locations of blood vessels and tissues surround bony prominences in the lower portion of a seated human body.

The present invention relates to a device and method for preventing and treating decubitus ulcers. FIGS. 1 through 3 illustrate the underlying anatomy and conditions that lead to the formation of decubitus ulcers. FIGS. 4 through 7 illustrate various aspects of the device and method according to the present invention.

As described above, a patient who is confined to a bed, a wheelchair or other types of furniture, and cannot move or be moved for prolonged periods of time, may be prone to decubitus ulcers (also referred to as bed sores or pressure sores) in the parts of their bodies having bony prominences that are subject to constant pressure when the parts of their bodies are resting or being constrained against a surface of the furniture. FIGS. 1 through 3 illustrates a basic bone structure, highlighting the bony prominences in the middle portion 5 of a person's body 1 over which pressure sores may form in tissue 3, 7 and 11 after a period of continuous and static pressure to the overlying tissue, when a patient is left or restrained to lie or sit in a bed or in a chair for prolonged periods of time without movement. Ischial decubitus ulcers or pressure sores may form in the tissue 3 covering the ischium 4 in the buttocks 2. Trochanteric decubitus ulcers or pressure sores may form in the tissue 7 covering the trochanters 6 (the broad flat bony prominence at the top of the femur 9) in the hips 8. Sacral decubitus ulcers or pressure sores may form in the tissue 11 covering the sacrum or sacral 12 in the area of the coccyx 10.

Decubitus ulcers 3, 7 and 11, may be prevented and/or treated with a device 20 that alleviates pressure on the tissue 3, 7 and 11 that is on and surrounds the bony prominences 4, 6 and 10 in a portion 5 of the body 1, while allowing blood to flow through the angiosomes 18 and blood vessels 5 in the portion 5 of the body 1, while the patient is resting or is confined or constrained in a particular position in or on a piece of furniture 13.

There are angiosomes 18 distributed throughout the middle portion 5 of the body 1, and through other parts or portions of the human body 1. An angiosome 18 is a three dimensional block of tissue supplied by a single source artery. The distribution of angiosomes 18 refers to a mapping of blood vessels 19 in a block of tissue, or the tree-line pattern or arborization of blood vessels in a certain area, e.g., in the body portion 5, or for the tissue 3, 7 and 11 on and surrounding the ischial or ischium 4, trochanteric 6, and sacral or sacrum 12. If external pressure cuts off the blood flow through one or more blood vessels 19 (e.g., venous return), then there may be a lack of nutrients and/or build up of toxins or waste product in the 3 dimensional block of tissue being serviced by those blood vessels 19 in a particular angiosome 18, which may lead to the formation of decubitus ulcers in the tissue. Thus, if any device that purports to relieve pressure on a part or portion 5 of the body 1 cuts off blood flow in an angiosome 18, the device may still affect the viability of the tissue being supplied by the blood vessels 19 in the angiosome 18.

Thus, a device 20 that alleviates pressure on areas of tissue 3, 7 and 11 while taking into account the location or distribution of angiosomes 18 and blood vessels 19 in a portion 5 of a body 1, will be able to alleviate pressure, while allowing for blood flow to continue in the portion 5 of the body 1. Since the mapping of blood vessels 19 or distribution of angiosomes 18 tends to be similar from person to person, it is possible to standardize a design of a device 20 based on the location or distribution of angiosomes 18 and blood vessels 19 in a portion 5 of the body 1, and use the device 20 on more than one person.

The device 20 illustrated in FIGS. 4 through 9 is configured to alleviate pressure on a middle portion 5 of the body 1 including the buttocks 2, hips 8 and coccyx 10. The device 20 includes a garment 25 and a pump 50 releasably attached or coupled or connected thereto to pump air, water or other fluids or gel-like substances and/or remove such fluids or substances from the garment 25 when the pump 50 is activated or actuated. The garment 25 is portable and configured to fit around the waist 15, and may be worn as a pair of shorts 26 on the body 1, alleviating pressure on and around the trochanteric bony prominences 6 in the hips 8, the ischial bony prominences 4 in the buttocks 2, and the sacral bony prominences 12 in the coccyx 10, and allowing blood flow based on the distribution of angiosomes 18 and the blood vessels 19 in the angiosomes 18 in the body portion 5.

The garment 25 provides pressure varying in a range sufficient for treating and/or preventing decubitus ulcers in the body portion 5. Unlike products that provide higher pressures that periodically cut off blood flow to simulate the pumping action of arterial inflow to prevent and/or treat deep vein thrombosis, the maximum pressure provided by the device 20 on the body portion 5 is set below the pressure for preventing and/or treating deep vein thrombosis.

The garment 25 includes sequential air technology to provide varying pressure on the body portion 5, based on the location or distribution of angiosomes 18 in the body portion 5 to allow for maximal blood flow throughout the angiosomes 18 in the body portion 5, including through the blood vessels 19 therein. The sequential air technology includes sequentially or periodically inflating and deflating channels 30 in garment 25. The channels 30 may be integrated or intertwined in a middle layer 22 or an outer layer 21 in the garment 25, and channels 30 may also refer to or include pockets or cushions.

The channels 30 are inflatable with a fluid, e.g., air or water, or with a gel-like substance, e.g., a silicon-based gel. The channels 30 are positioned in the garment 25 based on the location or distribution of angiosomes 18 in the body portion 5, and the blood vessels 19 in the body portion 5. The channels 30 are configured to be sequentially or periodically inflated and deflated. The channels 30 may provide a fluctuating pressure by continuously inflating or deflating, or the channels 30 may provide an otherwise varying pressure by remaining inflated and then deflated for certain periods of time, e.g., 5 minutes in each phase. The pressure applied by the inflated channels 30 on the body portion 5 and/or the pressure on the parts of the body portion 5 under the deflated channels 30 may be configured or set not to exceed the pressure that stops blood flow in the blood vessels, e.g., 32 mm Hg. The time periods and patterns of inflation and/or deflation of channels 30 may be configured to minimize the obstruction or reduction of blood flow in the blood vessels 19, and blood supply in the angiosomes 18 in the body portion 5.

Figure 5:
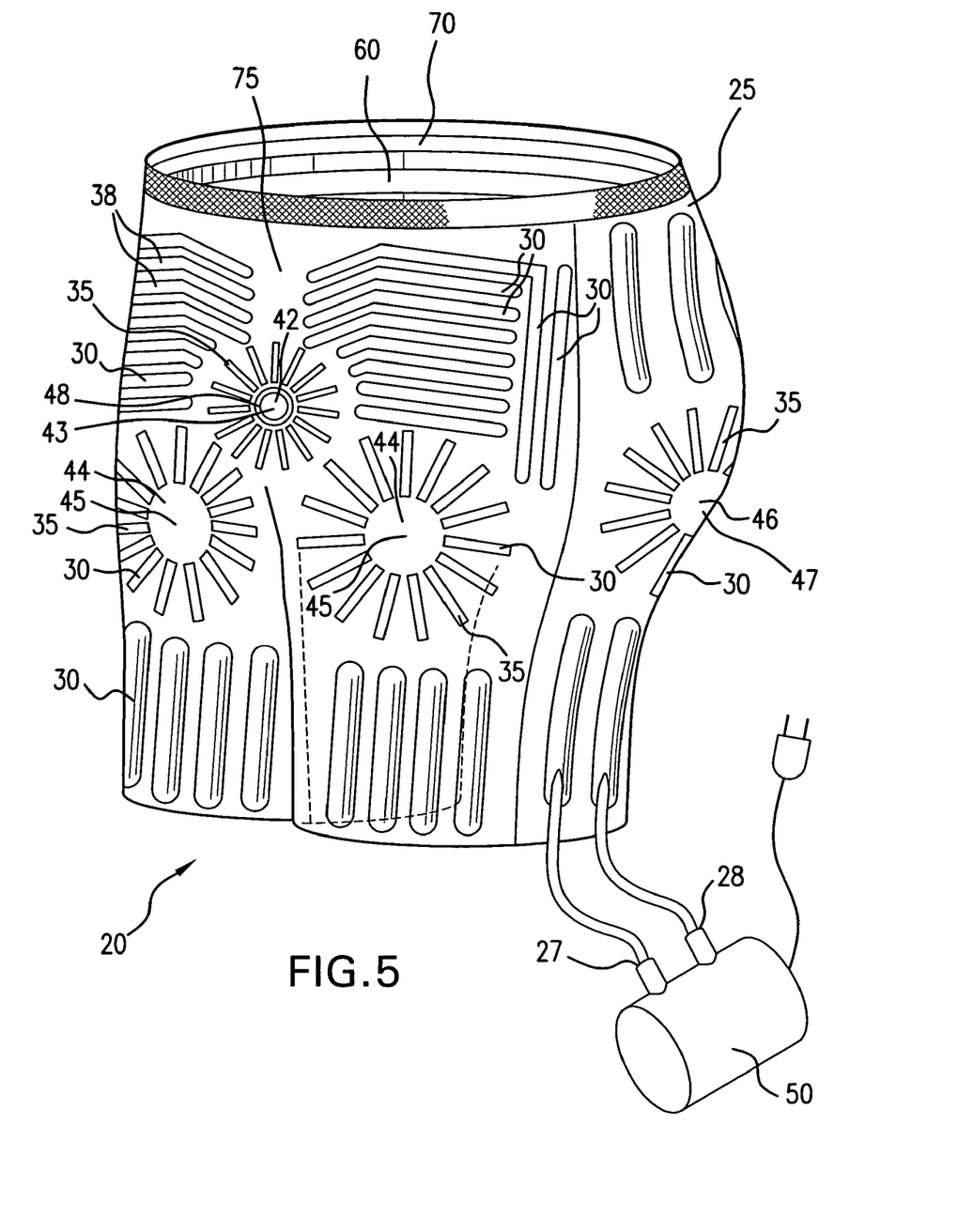
FIG. 5 illustrates a perspective rear view of the embodiment of the device for preventing and treating decubitus ulcers of FIG. 4.
Figure 8:
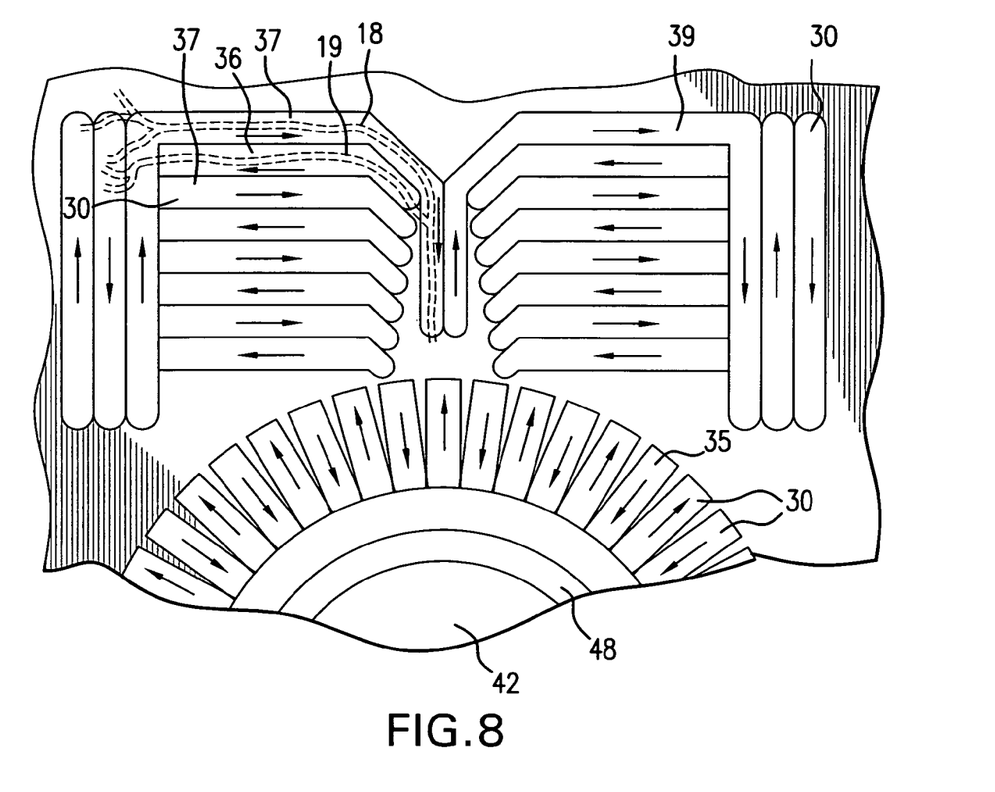
FIG. 8 illustrates a partial view of a portion of an embodiment of a device for preventing and treating decubitus ulcers and a partial view of the underlying blood vessels and angiosomes, according to the present invention.
Figure 9:
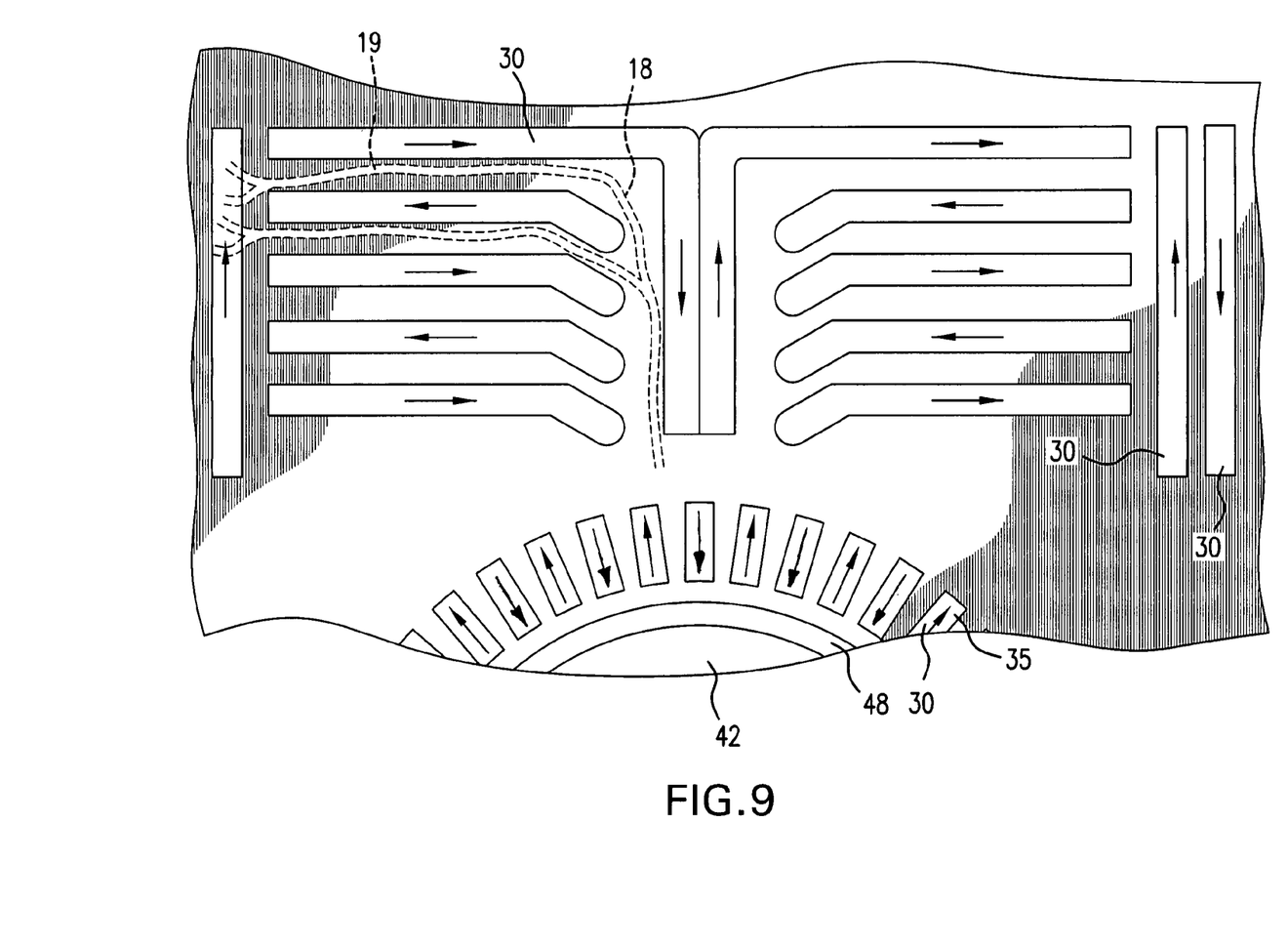
FIG. 9 illustrates a partial view of a portion of an embodiment of a device for preventing and treating decubitus ulcers and a partial view of the underlying blood vessels and angiosomes, according to the present invention.

Some of the channels 38 may be rib-shaped, parallel to one another, and arranged in a rib-like pattern, as illustrated in FIG. 5. Additionally, at least some of the channels 30 may be configured to be offset from the locations of angiosomes 18 or blood vessels 19 when the garment 25 is on the body portion 5. If the channels 30 were positioned in the garment 25 to cross blood vessels 19, then inflation of the channels 30 may obstruct or restrict blood flow through the blood vessels 19. In order to allow or promote maximal blood flow through the blood vessels 19 and angiosomes 18, some of the channels 30 may be positioned or configured to run adjacent to or parallel to blood vessels 19 in the angiosomes 18, as illustrated in FIGS. 8 and 9. The parallel placement of channels 30 helps to minimize any interruption or disturbance to the blood flow in the body portion 5, when the channels 30 are being inflated and/or deflated.

Some or all of the channels 30 may be spaced apart from one another, as illustrated in FIG. 9. Some or all of the channels 30 may be interwoven or intertwined, as illustrated in FIG. 8. Even if the channels are interwoven or intertwined, as illustrated in FIG. 8, there is no or little pressure (e.g., less then 32 mm Hg) on the blood vessels 19 under the deflated channels 36, in part due to the support provided by inflated channels 37, to allow blood flow, including venous return as well as arterial inflow to continue through the blood vessel 19.

The garment 25 may also include pressure relievers 44, 46 and 42 to protect the underlying tissue from any excess pressure, such as pressure from contact with a surface of the furniture 13. Pressure relievers 44, 46 and 42 may include or be made with a cushion or padding that alleviates some of the excess pressure on the tissue 3, 7 or 11, when in contact with a surface of the furniture 13. Alternatively, pressure relievers 44, 46 and 42 may lack any cushion or padding, but be surrounded by padded support, and the surrounding channels 30, so that the tissue thereunder does not come into contact or encounters minimal pressure from the garment 25 and from any surface on the furniture 13. The pressure relievers 44, 46 and 42 may not be inflated or inflatable to reduce or eliminate pressure placed on the underlying tissue.

Pressure reliever 44 is positioned in garment 25 to protect at least part or all of the tissue 3 in the area of the ischium bony prominence 4 in the buttocks 2. Pressure reliever 46 is positioned in garment 25 to protect at least part or all of the tissue 7 in the area of the trochanteric bony prominence 6 in the hips 8. Pressure reliever 42 is positioned in garment 25 to protect at least part or all of the tissue 11 in the area of the sacral bony prominence 12 in the coccyx 10. The garment 25 may include a sacral ring 48 to surround or encircle pressure reliever 42. The sacral ring 48 may provide extra support for the garment 25. For example, if the sacral ring 48 is integrated with the outer layer 21, the sacral ring 48 may maintain the integrity of the garment 10 around the sacrum 12. The sacral ring 48 may be made of a rigid material or a more flexible material, such as, e.g., plastic. Alternatively, the garment 25 may have no sacral pressure reliever 42, but the tissue in the sacral area 11 may be protected from excess pressure by the sacral ring 48 alone, for example, if it is of sufficient thickness to protect tissue 11 from direct contact with a surface of furniture 13.

Some of the channels 30 in the garment 25 may include one or more channels 35 configured around the pressure relievers 44, 46 and 42. The channels 35 may be configured or positioned to be offset from the center of the tissue on and surrounding a bony prominence, e.g., centers 45, 47 and 43 of the areas of tissue 3, 7 and 11, covering the ischium, trochanteric and sacral bony prominences 4, 6 and 12, in the region of the buttocks 2, hips 8 and coccyx 10, respectively, also referred to as the ischial, trochanteric and sacral areas of the body portion 5. The channels 35 may be referred to as additional channels, and may be positioned to extend radially from the centers 45, 47 and 43 when the garment 25 is on the body portion 5. The channels 35 arranged radially around the pressure relievers 44, 46 and 42, and around the tissue centers 45, 47 and 43, may extend radially through the part of tissue 3, 7 and 11 that surround the centers 45, 47 and 43 (which may also be referred to as pressure centers). The remainder of the channels 30 may be positioned in rib-like patterns outside of the pressure relievers 44, 46 and 42, and the additional channels 35 positioned around the pressure relievers 44, 46 and 42.

The device 20 also includes a pump 50 releasably connectable to the garment 25 via one or more valves or ports on garment 25. The pump 50 may be small and lightweight, to be portable, and may be configured to be releasably attachable to one or more pieces of furniture (including a chair 13, or for example, the intravenous pole), or directly to the person using the garment 25, e.g., as on a belt around the waist 15.

Figure 4:
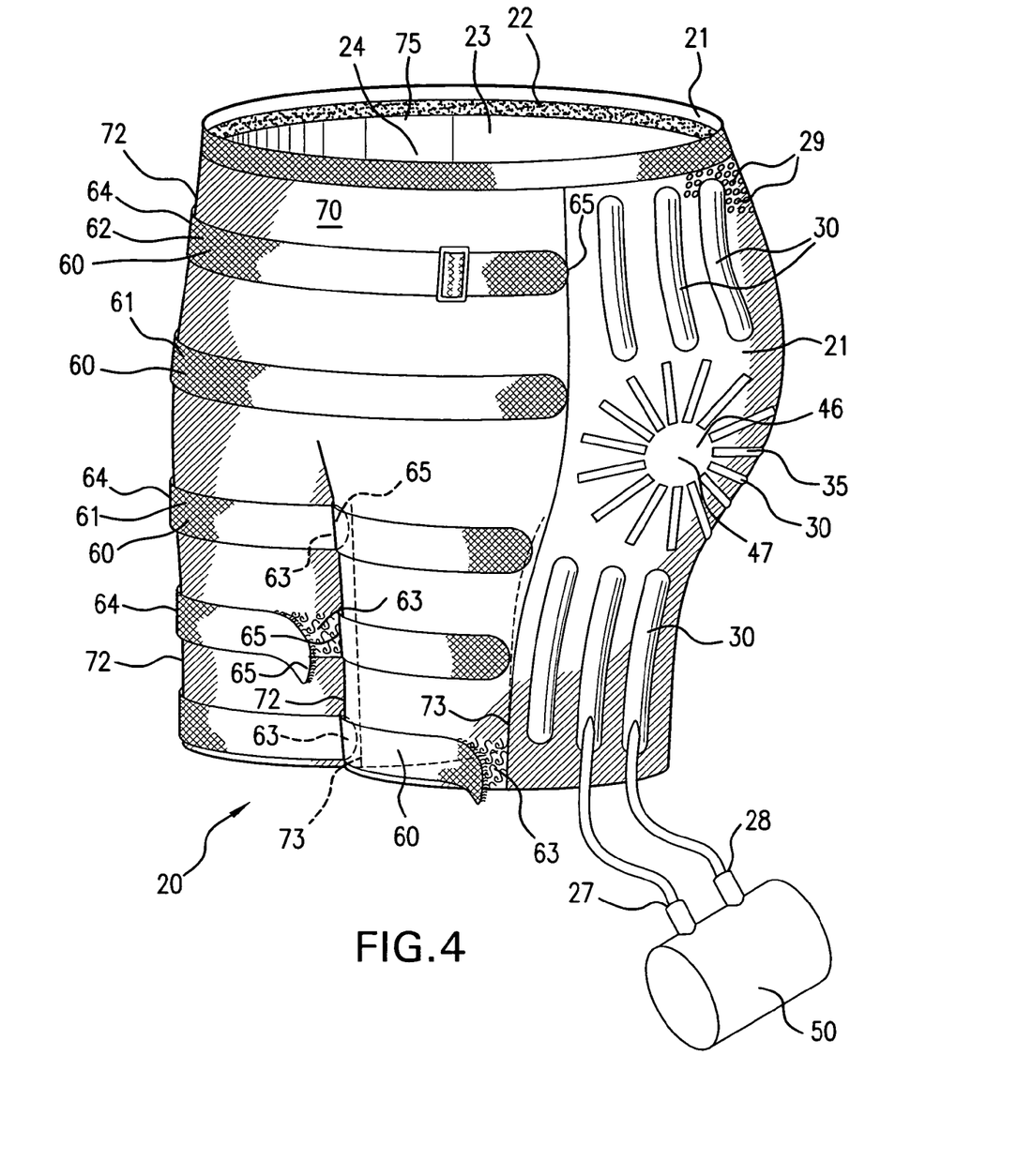
FIG. 4 illustrates a perspective frontal view of an embodiment of a device for preventing and treating decubitus ulcers according to the present invention.
Figure 6:
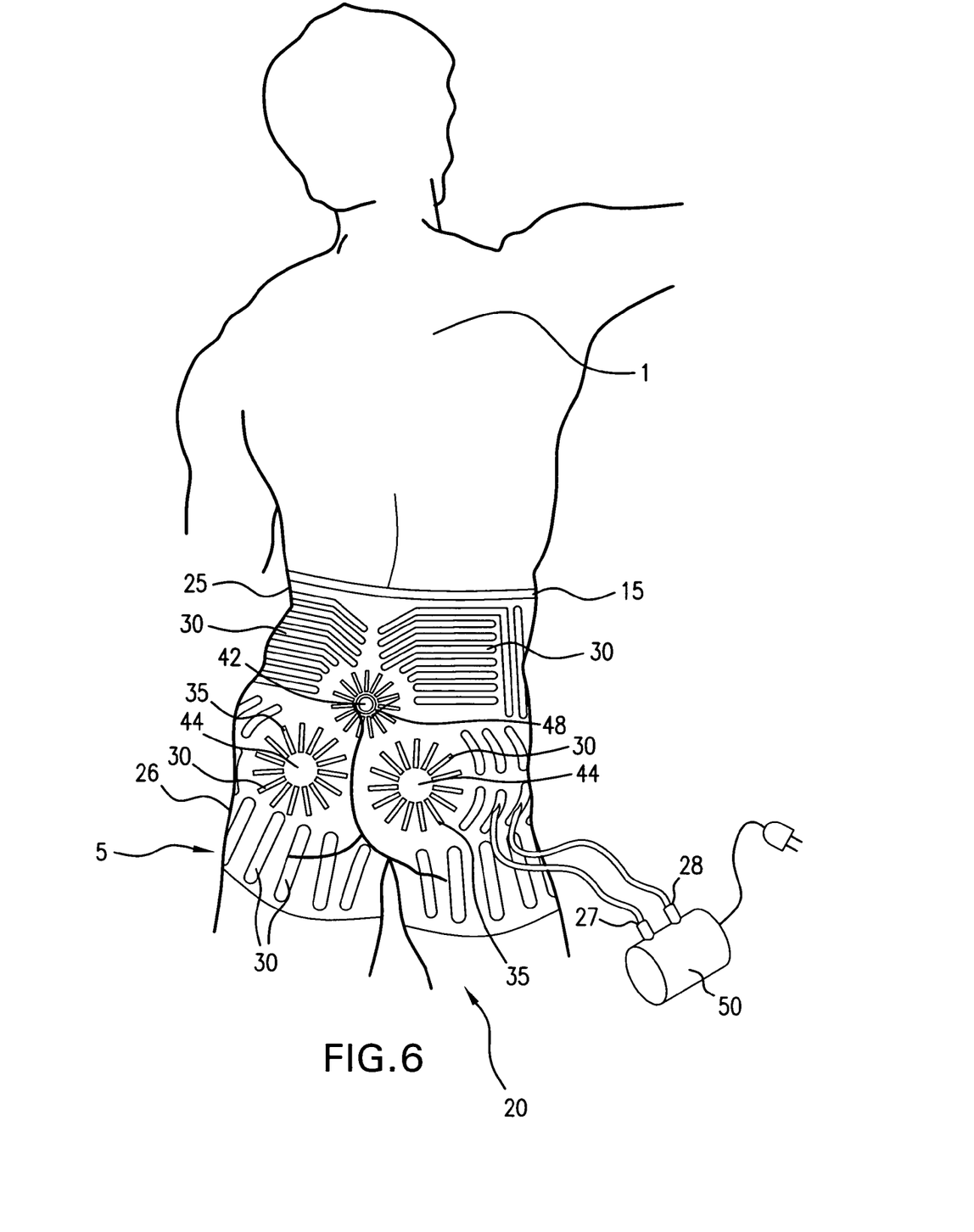
FIG. 6 illustrates a perspective rear view of a person in a standing position wearing the embodiment of the device for preventing and treating decubitus ulcers of FIG. 4.
Figure 7:
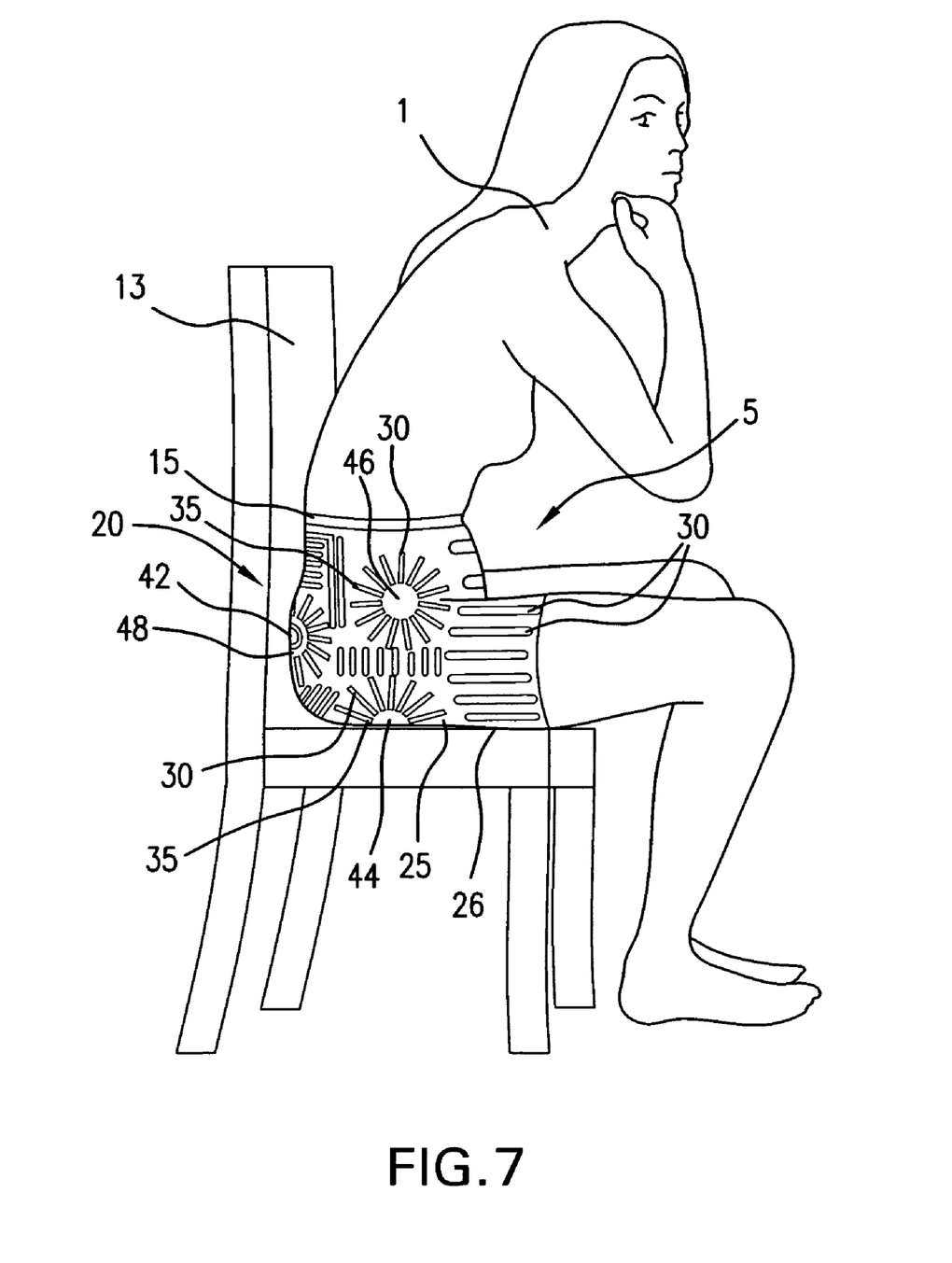
FIG. 7 illustrates a perspective frontal view of a person in a seated position wearing the embodiment of the device for preventing and treating decubitus ulcers of FIG. 4.

As illustrated in FIGS. 4 through 6, pump 50 is releasably connectable to ports 27 and 28 on garment 25. The pump 50 is configured to periodically or sequentially inflate and deflate one or more of the channels 30 in the garment 25 through valves or ports 27 and 28 on garment 25, e.g., by pumping and/or removing air, water or other fluids or gel-like substances into and/or out of the channels 30 through ports 27 and 28. The pump 50 may be configured to be able to regulate the amount of fluids or substance being pumped or removed from channels 30. The pump 50 may also be configured to time the periods for each of the inflation and deflation cycles. The pump 50 may be configured to inflate and deflate all of the channels 30 at the same time. Alternatively, the pump 50 may be configured to inflate one subset of channels 30 through port 27 while deflating another subset of channels 30 through port 28. As illustrated in FIGS. 8 and 9 with arrows indicating directions of fluid movement, one subset of channels 37 may be inflated through port 27 while another subset of channels 36, alternating between channels 37, are being deflated through port 28.

Alternatively, the first subset of channels 30 may be configured to be one side of the garment 25, and the second subset of channels 30 may be configured to be on another side of the garment 25. The sequential or periodic inflation and/or deflation of the first and second subsets of channels 30 under this configuration provides a rocking motion, and may be implemented to periodically move the patient from one position to another. The pump 50 may be supplied with additional ports (not shown), so that the pump 50 may be configured to act on one set of channels 30 at a time, for example, leaving a third subset of channels entirely deflated if it is on a portion of the body not in contact with a piece of furniture 13. In any case, alternately inflating and deflating different portions of garment 25 or different subsets of channels 30 according to different patterns will prevent pressure from inflated channels remaining on any specific location of the body portion 5 for an extended amount of time.

The garment 25 itself may be made with a durable washable material, e.g., plastic. The garment 25 may be configured with layers, as illustrated in FIG. 4. The channels 30 may be integrated into a middle layer 22 of garment 25. Outer layer 21 may provide a protective plastic covering over the channels 30 and the remainder of the garment 25. The outer layer 21 may have holes or pores 29 to allow air to pass through to and from the middle layer 22, the inner layer 23 and the body portion 5. Outer layer 21 may be detachable from the rest of the garment 25, to be washed or rinsed off, or replaced.

The inner layer 23 may include a liner or lining 24 that is made with a breathable or softer or hypoallergenic fabric or other material, e.g., cotton, nylon, polyester, rayon, or lycra, or a combination or blend of any two or more of the foregoing materials. The lining 24 may be releasably attachable to the inner layer 23 of the garment 25. The lining 24 may cover all or part of the inner layer 23 of the garment 25. The lining 24 may be removable to be washable or disposable, and in any case, replaceable.

The garment 25 may be releasably attachable to the body portion 5 via one or more straps 60 on a front side 70 of the garment 25, as illustrated in FIG. 4. The straps 60 may be elastic bands 61 or otherwise adjustable, as adjustable band 62. The straps 60 may be made with a material including cotton, to increase the comfortability of the device 20. The straps 60 may make it easier for the garment 25 to be placed on or removed from the body portion 5.

The straps 60 may be spaced apart from one another in order to permit the frontal area of the body portion 5 to remain exposed for further examination and follow up by a doctor, nurse or other care giver. The straps also provide a way of attaching the garment 25 to the body portion 5, without unnecessarily covering the frontal area of the body portion 5. The straps 60 may allow the person wearing the garment 25 to be more comfortable and cooler, then if the frontal area of the body portion 5 were fully covered as well.

The straps 60 may be permanently attached at a distal end 64 to a first side 72 of the garment 25, and releasably attached at a proximal end 65 to an opposite side 73 of the front side 70 of the garment 25. The straps 60 may be releasably attachable with velcro 63 on sides 73, or with buttons, snaps, zippers and other modes of releasably attaching or fastening the straps 60 to the sides 73 of the garment 25.

Figure 10:
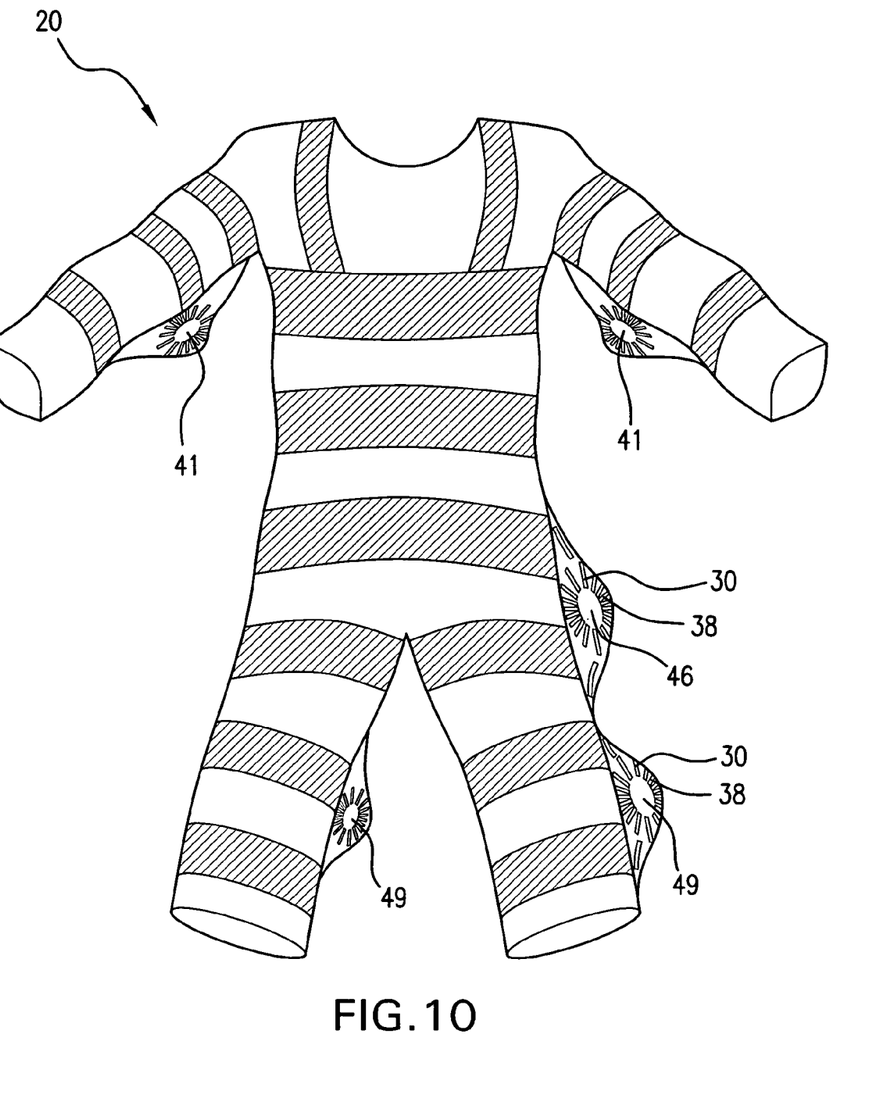
FIG. 10 illustrates a frontal perspective view of an embodiment of a device for preventing and treating decubitus ulcers according to the present invention.
Figure 11:
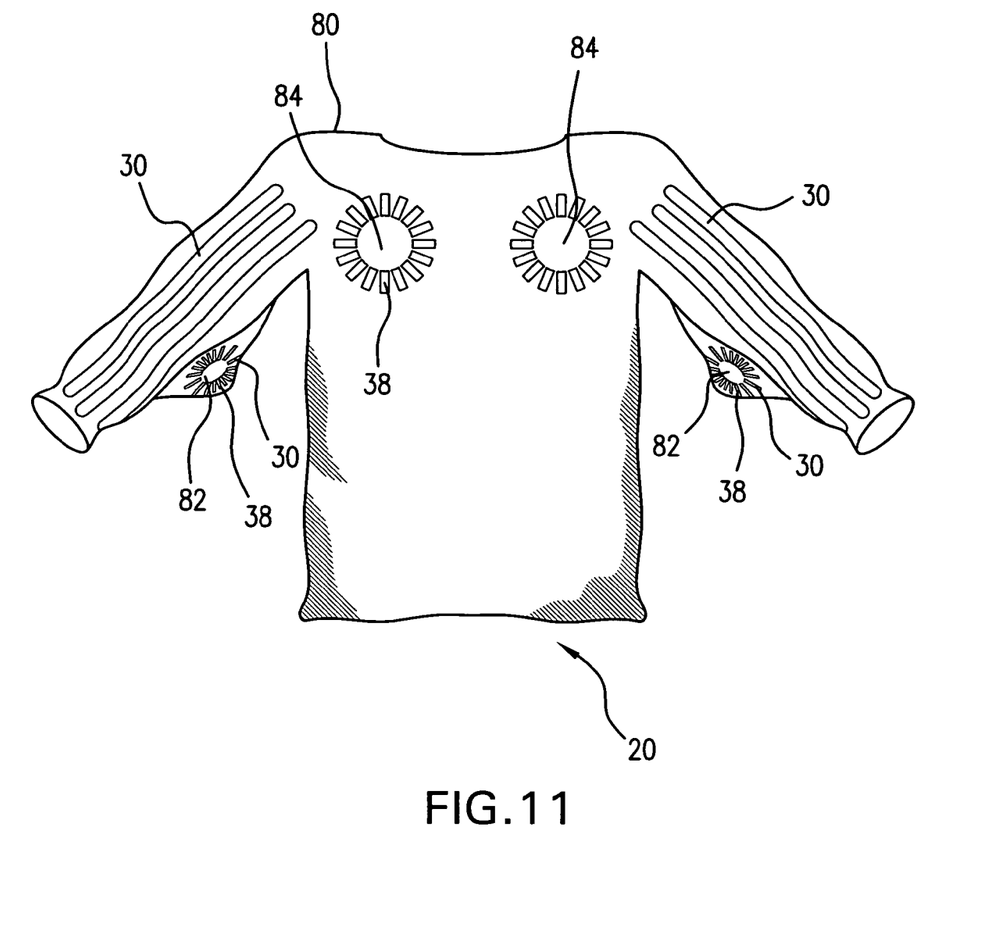
FIG. 11 illustrates a rear perspective view of an embodiment of a device for preventing and treating decubitus ulcers according to the present invention.

The device 20 illustrated in FIGS. 4 through 9 is configured for body portion 5, including the buttocks 2, hips 8, and coccyx 10. As illustrated in FIG. 10, the device 20 may extend further down the legs and further along the arms, with channels 30 and pressure relievers 41 and 49 for the elbows and calves. As illustrated in FIG. 11, device 20 may include a garment 80 configured to fit on an upper body portion, with shoulder blade pressure relievers 84, and with elbow pressure relievers 82. The device 20 may be configured with pressure relievers in a variety of locations, and a variety of patterns for the distribution of channels 30, depending on the position of the body 1, the type of furniture 13, and other conditions.

In the preceding specification, the present invention has been described with reference to specific exemplary embodiments thereof. It will, however, be evident that various modifications and changes may be made thereunto without departing from the broader spirit and scope of the present invention as set forth in the claims that follow. The specification and drawings are accordingly to be regarded in an illustrative rather than restrictive sense.

What is claimed is:

1. An apparatus comprising:
   a portable garment configured to be placed on a portion of a body to provide a varying pressure on the portion, the provided pressure varying within a range sufficient for at least one of treating and preventing a decubitus ulcer in the portion;
   a plurality of channels positioned in the garment based on a location of at least one angiosome in the portion, the plurality of channels comprising at least a first subset and at least a second subset; and
   an inflation-deflation means connected to the at least first subset and the at least second subset of the plurality of channels, the inflation-deflation means for at least one of:
   (i) inflating the at least first subset while deflating the second subset, to maintain the pressure within the range;

and (ii) deflating the at least first subset while inflating the second subset, to maintain the pressure within the range.

2. The apparatus according to claim 1, wherein the garment includes at least one channel positioned in the garment based on an angiosome distribution in the portion.

3. The apparatus according to claim 1, wherein a maximum of the provided pressure is set below a level sufficient for treating deep vein thrombosis.

4. The apparatus according to claim 1, wherein the garment includes sequential air technology providing the varying pressure on the portion based on angiosome distribution in the portion to allow for maximal blood flow in the portion.

5. The apparatus according to claim 1, wherein the channels are positioned in the garment based on angiosome distribution in the portion.

6. The apparatus according to claim 1, wherein the channels are configured to be sequentially inflated and deflated.

7. The apparatus according to claim 6, wherein the channels are configured to be inflated with at least one of:
a fluid, air, water, and a gel-like substance.

8. The apparatus according to claim 1, wherein the channels include at least one channel configured to be offset from a location of an angiosome when the garment is on the portion.

9. The apparatus according to claim 1, wherein the channels include at least one channel configured to be adjacent and/or parallel to a blood vessel in an angiosome when the garment is on the portion.

10. The apparatus according to claim 1, wherein the channels include at least one channel configured to be offset from a center of an area of tissue on a bony prominence and to extend radially from the center of the tissue area when the garment is on the portion.

11. The apparatus according to claim 1, wherein the channels include at least one channel configured to be offset from a center of an area of tissue on a bony prominence and to extend radially away from the center of the tissue area when the garment is on the portion.

12. The apparatus according to claim 1, wherein the garment includes at least one additional channel configured to extend radially away from a pressure center when the garment is on the portion.

13. The apparatus according to claim 12, wherein the additional channels are configured to be radially oriented in the garment to extend radially through an area of tissue surrounding the pressure center.

14. The apparatus according to claim 1, wherein the channels include at least one channel parallel to another channel.

15. The apparatus according to claim 1, wherein the portion of the body includes at least one of the buttocks, hips and coccyx.

16. The apparatus according to claim 15, wherein the garment includes a pressure reliever located in at least one of:
an ischial area of the buttocks, a trochanteric area of the hips, and a sacral area of the coccyx.

17. The apparatus according to claim 15, wherein the portion of the body includes at least part of the legs.

18. The apparatus according to claim 15, wherein a back side of the garment is configured to cover the buttocks, and at least part of legs, back and arms of a patient wearing the garment.

19. The apparatus according to claim 1, wherein the channels are positioned in the garment based on locations of a plurality of angiosomes in the portion.

20. The apparatus according to claim 1, wherein the inflation-deflation means comprises: a pump releaseably connectable to the garment, the pump being configured to sequentially inflate and/or deflate at least one channel in the garment.

21. The apparatus according to claim 20, wherein the pump is configured to inflate and/or deflate the first subset.

22. The apparatus according to claim 21, wherein the pump is configured to inflate and/or deflate the second subset.

23. The apparatus according to claim 22, wherein the pump is configured to deflate the second subset while inflating the first subset and/or inflate the second subset while deflating the first subset.

24. The apparatus according to claim 23, wherein the plurality of channels includes a third subset configured to remain deflated while the first and second subsets are being sequentially inflated and deflated such that the provided pressure in the at least one deflated subset on the portion is less than or equal to about 32 mm Hg.

25. The apparatus according to claim 22, wherein at least one channel in the first subset is at least one of:
positioned between at least two channels in the second subset, and intertwined with at least one channel in the second subset.

26. The apparatus according to claim 22, further comprising: a first port connected to the first subset of channels; and a second port connected to the second subset of channels.

27. The apparatus according to claim 26, wherein the pump is releasably connectable to the first port and inflates the first subset of channels through the first port.

28. The apparatus according to claim 27, wherein the pump is releasably connectable to the second port and deflates the second subset of channels through the second port.

29. The apparatus according to claim 20, wherein the pump is at least one of: portable and configured to be releasably attachable to at least one of a piece of furniture and a person using the garment.

30. The apparatus according to claim 1, wherein the garment includes at least one pressure reliever for protecting an area on the portion from excess pressure.

31. The apparatus according to claim 30, wherein the pressure reliever is positioned to protect from excess pressure at least one of:
a bony prominence on the portion, at least part of a trochanteric area, at least part of an ischial area, at least part of a sacral area.

32. The apparatus according to claim 31, wherein the garment includes a sacral ring to surround the pressure reliever to protect at least part of a sacral area.

33. The apparatus according to claim 30, wherein the presser reliever includes at least one of a cushion and a padding.

34. The apparatus according to claim 30, wherein the garment includes the plurality of channels positioned around the pressure reliever, and the plurality of channels are operable to be sequentially inflated and deflated in the garment such that the provided pressure in the deflated channels on the portion is less than or equal to about 32 mm Hg.

35. The apparatus according to claim 34, wherein at least one additional channel extends radially from a center of the pressure reliever, and the at least one additional channel is operable to be sequentially inflated and deflated in the garment such that the provided pressure in the deflated channels on the portion is less than or equal to about 32 mm Hg.

36. The apparatus according to claim 35, wherein the plurality of channels are positioned in rib-like patterns in the garment outside of the pressure relievers and the at least one additional channel is positioned around the pressure relievers.

37. The apparatus according to claim 36, wherein at least some of the rib-like positioned channels are at least one of:

intertwined with each other, and spaced apart from each other.

38. The apparatus according to claim 36, wherein the plurality of channels are positioned around the pressure relievers and the at least one additional channel.

39. The apparatus according to claim 1, wherein the garment is made with at least one of:
a durable material, a washable material, and plastic.

40. The apparatus according to claim 1, wherein the garment includes a lining covering at least part of an interior of the garment.

41. The apparatus according to claim 40, wherein the lining is at least one of:
removable, washable, disposable, replaceable, and a fabric;
wherein the fabric is made with at least one of:
cotton, nylon, polyester, rayon, lycra, and a hypoallergenic material.

42. The apparatus according to claim 1, wherein the garment includes an inner layer and an outer layer.

43. The apparatus according to claim 42, wherein the outer layer has pores.

44. The apparatus according to claim 43, wherein the inner layer and the outer layer are detachable from a remainder of the garment.

45. The apparatus according to claim 44, wherein the channels are in a middle layer between the inner layer and outer layer.

46. The apparatus according to claim 1, wherein the garment includes cushions configured to be sequentially inflated and deflated to alleviate pressure on the portion such that the provided pressure in the deflated cushions on the portion is less than or equal to about 32 mm Hg.

47. The apparatus according to claim 46, wherein the portion includes at least one of a sacrum, ischial and trochanter areas of a coccyx, buttocks, and hips.

48. The apparatus according to claim 1, wherein the garment is portable.

49. The apparatus according to claim 1, wherein the garment is configured to be worn in a coccygeal area of a body.

50. The apparatus according to claim 1, wherein the garment includes straps on a front side of the garment to releasably attach the garment to the portion.

51. The apparatus according to claim 50, wherein the straps are elastic bands.

52. The apparatus according to claim 50, wherein the straps are at least one of: adjustable and spaced apart from one another.

53. The apparatus according to claim 50, wherein the straps are attached to one side of the front side of the garment, and are releasably attached to an opposite side of the front side of the garment via at least one of a velcro, button, snap and zipper fastening.

54. The apparatus according to claim 1, wherein the garment includes an adjustable band configured to hold the garment to a body.

55. The apparatus according to claim 54, wherein the adjustable band has a proximal end and a distal end, the adjustable band being releasably attached to the garment at the proximal end and permanently attached at the distal end.

56. An apparatus comprising: a device including a plurality of inflatable channels, the plurality of channels comprising a portable garment having at least a first subset and at least a second subset, and an inflation-deflation means connected to the at least first subset and the at least second subset of the plurality of channels, the inflation-deflation means for at least one of:

(i) inflating the at least first subset while deflating the second subset to provide a rocking motion for moving a patient from one position to another; and (ii) deflating the at least first subset while inflating the second subset to provide a rocking motion for moving a patient from one position to another.

57. The apparatus according to claim 56, wherein the at least first subset is positioned on a first side of the apparatus and the at least second subset is positioned on a second side of the apparatus, and the at least first and second subsets are operable to be sequentially inflated and deflated such that the movement of the patient prevents pressure from the inflated subset remaining on any specific location of a body portion for an extended amount of time.

58. The apparatus according to claim 57, wherein the inflation-deflation means comprises a pump releasably connected to the device, the pump being configured to pump and remove air from the inflatable subsets.

59. A garment for treating and preventing decubitus ulcers around at least one of a coccygeal, buttocks and hip areas of a body comprising: at least one cushion positioned in the garment as a function of angiosome distribution for the at least one sacrum, ischial and trochanter areas, the at least one cushion comprising at least a first subset of at least one pocket or cushion and at least a second subset of at least one pocket or cushion and being operable to provide a varying pressure on the areas, the provided pressure varying within a range sufficient for at least one of treating and preventing a decubitus ulcer in the at least one sacrum, ischial and trochanter areas; and at least one adjustable band removably attaching the garment to the body, wherein the at least first subset and the at least second subset of the garment connect to an inflation-deflation means for at least one of: (i) inflating the at least first subset while deflating the second subset; and (ii) deflating the at least first subset while inflating the second subset.

60. An apparatus for treating and preventing decubitus ulcers around at least one of a coccygeal, buttocks and hip areas of a body comprising: a garment including a plurality of inflatable channels, the plurality of channels comprising at least a first subset and a second subset configured to be alternately inflated and deflated in order to provide at least one varying pressure on a body portion, the provided pressure varying within a range sufficient for at least one of treating and preventing a decubitus ulcer in the portion; at least one pressure reliever; a plurality of additional channels positioned around the at least one pressure reliever for protecting an area on the portion from excess pressure, the channels and the at least one pressure reliever being positioned in the garment based on angiosome distribution for sacrum, ischial and trochanter regions in the coccygeal, buttocks and hip areas; and a pump releasably connectable to the garment, the pump being configured to pump and remove air from the inflatable channels in the garment, wherein:
at least one of (i) the at least first subset is operable to be inflated while the second subset is deflated; and (ii) the at least first subset is operable to be deflated while the second subset is inflated, to maintain the pressure within the range, and
each of the plurality of additional channels: (i) is offset from a center of the pressure reliever, (ii) extends radially away from the center of the pressure reliever, and (iii) is operable to be inflated and/or deflated such that the pressure reliever provides the at least one varying pressure on the portion.

61. The apparatus according to claim 1, wherein the provided pressure in the deflated subset on the portion is less than or equal to about 32 mm Hg.

62. The apparatus according to claim 1, wherein the at least first and second subsets are operable to be sequentially inflated and deflated in the garment such that the provided pressure in the deflated subset on the portion is less than or equal to about 32 mm Hg.

63. The apparatus according to claim 1, wherein the inflation-deflation means comprises: a pump releaseably connectable to the garment, the pump being configured to inflate the first subset while deflating the second subset and/or the pump being configured to deflate the first subset while inflating the second subset, to maintain the pressure within the range.

64. The apparatus according to claim 23, wherein the pump is configured to sequentially inflate and deflate the first and second subsets such that the provided pressure in the deflated subset on the portion is less than or equal to about 32 mm Hg.

65. The apparatus according to claim 25, wherein the pump is configured to sequentially inflate and deflate the first and second subsets such that the provided pressure in the deflated subset on the portion is less than or equal to about 32 mm Hg.

66. The apparatus according to claim 57, wherein the plurality of channels includes a third subset configured to remain deflated while the first and second subsets are being sequentially inflated and deflated to move the patient, wherein the third subset is on a portion of the body not in contact with a piece of furniture.

67. The apparatus according to claim 58, wherein the plurality of channels includes a third subset configured to remain deflated while the pump sequentially inflates and deflates the first and second subsets move the patient, wherein the third subset is on a portion of the body not in contact with a piece of furniture.

68. The apparatus according to claim 58, wherein the pump is configured to sequentially inflate and deflate the inflatable subsets such that the resulting movement of the patient prevents pressure from the inflated subset remaining on any specific location of a body portion for an extended amount of time.

69. The apparatus according to claim 58, wherein the pump includes additional ports to inflate or deflate one subset at a time.

70. The garment according to claim 59, wherein the provided pressure in the deflated subset on the at least one areas is less than or equal to about 32 mm Hg.

71. The garment according to claim 59, wherein the at least first and second subsets are operable to be sequentially inflated and deflated in the garment such that the provided pressure in the deflated subset on the at least one areas is less than or equal to about 32 mm Hg.

72. The garment according to claim 71, further comprising a pump operable to sequentially inflate and deflate the first and second subsets such that the provided pressure in the deflated subset on the at least one areas is less than or equal to about 32 mm Hg.

73. The garment according to claim 72, wherein the at least one cushion further comprises a third subset configured to remain deflated while the first and second subsets are being sequentially inflated and deflated such that the provided pressure in the at least one deflated subset on the at least one areas is less than or equal to about 32 mm Hg.

74. The apparatus according to claim 60, wherein the provided pressure in the deflated subset and the at least one deflated additional channel on the portion is less than or equal to about 32 mm Hg.

75. The garment according to claim 60, wherein the at least first and second subsets and the at least one additional channel are operable to be sequentially inflated and deflated in the garment such that the provided pressure in the deflated subset and the at least one deflated additional channel on the portion is less than or equal to about 32 mm Hg.

76. The garment according to claim 60, wherein the pump is operable to sequentially inflate and deflate the at least first and second subsets and the at least one additional channel such that the provided pressure in the deflated subset and the at least one deflated additional channel on the portion is less than or equal to about 32 mm Hg.

77. The garment according to claim 76, wherein the plurality of channels further comprises a third subset configured to remain deflated while the first and second subsets are being sequentially inflated and deflated such that the provided pressure in the at least one deflated subset on the portion is less than or equal to about 32 mm Hg.

* * * * *